United States Patent [19]

Asanuma et al.

[11] Patent Number: 5,347,048
[45] Date of Patent: Sep. 13, 1994

[54] PROCESS FOR PRODUCING (±)-2,5,5,8A-TETRAMETHYL-1-(CARBOXYMETHYL)-2-HYDROXYDECALIN

[75] Inventors: Goro Asanuma, Kurashiki; Yoshin Tamai, Shibata, both of Japan

[73] Assignee: Kuraray Co., Ltd., Kurashiki, Japan

[21] Appl. No.: 116,605

[22] Filed: Sep. 7, 1993

Related U.S. Application Data

[62] Division of Ser. No. 995,978, Dec. 23, 1992, Pat. No. 5,290,955.

[30] Foreign Application Priority Data

Dec. 29, 1991 [JP] Japan .................................. 3-358777
Dec. 29, 1991 [JP] Japan .................................. 3-358778

[51] Int. Cl.$^5$ .............................................. C07C 61/12
[52] U.S. Cl. ..................................... 562/501; 562/497
[58] Field of Search ................................ 562/497, 501

[56] References Cited

U.S. PATENT DOCUMENTS 4,845,272 7/1989 Nohira et al. .
4,904,822 2/1990 Nohira et al. .
5,066,826 11/1991 Nohira et al. .

*Primary Examiner*—Michael L. Shippen
*Attorney, Agent, or Firm*—Oblon, Spivak, McClelland, Maier & Neustadt

[57] ABSTRACT

A process for producing (±)-2,2,2,5a-tetramethyl-1-(carboxymethyl)-2-hydroxydecalin, comprising the steps of allowing a carbonate of dihydro-β-vinyl-ionol to react with carbon monoxide in the presence of a palladium catalyst to form β-monocyclohomofarnesic acid, cyclizing said β-monocyclohomofarnesic acid in the presence of an acid catalyst to form (±)-norambreinolid, and hydrolyzing said (±)-norambreinolide to form (±)-2,5,5,8a-tetramethyl-1-(carboxymethyl)-2-hydroxydecalin.

18 Claims, No Drawings

PROCESS FOR PRODUCING (±)-2,5,5,8A-TETRAMETHYL-1-(CARBOXYMETHYL)-2-HYDROXYDECALIN

This is a division, of application Ser. No. 07/995,978, filed on Dec. 23, 1992, now U.S. Pat. No. 5,290,955.

BACKGROUND OF THE INVENTION

1. Field of the Invention

This invention relates to a process for producing (−)-3a, 6,6,9a-tetramethyl-dodecahydronaphtho[2,1-b]furan (hereinafter "L-ambrox") represented by Formula (1):

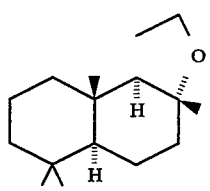

which is an important perfumery substance having an excellent aroma of an amber. More particularly, this invention relates to a process for producing the L-ambrox by the use of a (−)-2,5,5,8a-tetramethyl-1-(carboxymethyl)-2-hydroxydecalin (hereinafter "(−)HC acid") represented by Formula (10a):

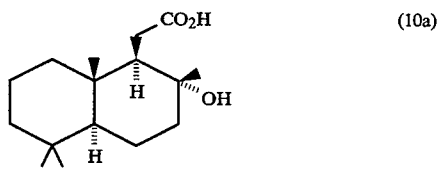

as a starting material, at a low cost and in an industrial scale. This invention also relates to a process for optically resolving (±)-2,5,5,8a-tetramethyl-1-(carboxymethyl)-2-hydroxydecalin, which is a mixture of equal quantities of (−)HC acid and (+)-2,5,5,8a-tetramethyl-1-(carboxymethyl)-2-hydroxydecalin (hereinafter "(+)HC acid"), into (−)HC acid and (+)HC acid to thereby obtain the optically active (−)HC acid or (+)HC acid represented by Formula (10b):

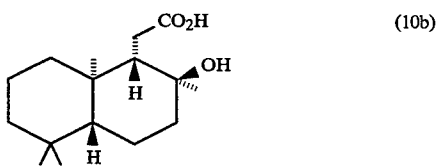

which is useful as a starting material for synthesizing a compound having a trimethyl-transdecalin skeleton represented by Formula (A):

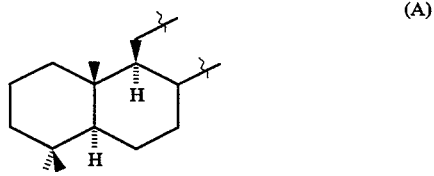

having a physiological activity or a characteristic aroma, as exemplified by the L-ambrox or the like.

2. Description of the Related Art

Optically active substances having a trimethyl-transdecalin skeleton naturally occur and many of such substances are known to have useful physiological activities or characteristic aromas [Von Gerhard Buchbauer et al., Chemiker Zeitung, 112, 319–333 (1988)]. For example, the optically active (−)-3a,6,6,9a-tetramethyl-dodecahydronaphtho[2,1-b]furan (common name: L-ambrox) represented by Formula (1) is known as an important substance having the aroma of an amber.

As processes for producing the L-ambrox, the following processes have been hitherto proposed.

Process (a)

An optically active substance (−)-sclareol present in an essential oil of naturally occurring Salvia sclarea is used as a starting material. This is subjected to chromium oxidation to produce (+)-norambreinolide [Helv. Chi,. Acta., 14, 570, (1931)], and then the (+)-norambreinolide is reduced, followed by cyclization [Dragoco Report, 11/12, 276–283 (1979)].

Process (b)

A process in which an optically active substance (+)-manool is used as a starting material (Japanese Patent Application Laid-open No. 62-39539).

Process (c)

A process in which an optically active substance L-abietic acid is used as a starting material [M. Ohno et al., Tetrahedron Letters, 28, 2863 (1987)].

Process (d)

A process in which an optically active substance L-levopimaric acid is used as a starting material [Y. Nishi et al., J. Jpn. Oil. Chem. Soc., 38, 276 (1989)].

The process (a), however, has been involved in the problem that the starting material used, Salvia sclarea oil, is unsuitable as the starting material for producing the L-ambrox in an industrial scale since it can be obtained from vegetables cultivated only in limited areas having particular climate or natural features and is relatively expensive. In addition, this process has also had the problem that a heavy metal oxidizing agent such as potassium permanganate or chromic acid, which is not suited for its industrial use because of the problem of environmental pollution caused by waste liquor, is used as an oxidizing agent when the (−)-sclareol is decomposed by oxidation.

The process (b) is reported to be a little more advantageous than the process (a) in view of the supply of starting materials, but has had the problem that a heavy metal oxidizing agent is also used in the step of oxidative decomposition.

The processes (c) and (d) are considered to be more advantageous than the processes (a) and (b) in view of the supply of starting materials, but has had the problem that it requires a number of reaction steps and use of expensive reagents and involves many reaction procedures unsuitable for their industrial application. In this regard, when a compound having the optically active trimethyl-transdecalin skeleton including L-ambrox is produced, asteric structure to which the optical activity thereof is attributable must be selectively realized for the compound. For that purpose, a variety of production processes have been hitherto proposed. For example, it is known to use a method in which the final compound is produced using an optically active starting material obtainable from natural sources or a method in which the desired optically active compound is produced by utilizing enzymatic reaction or other reaction similar thereto by the use of an optically inactive starting material.

However, the conventional method of producing the final compound by the use of an optically active starting material has been involved in the problem that optically active starting materials can be obtained with difficulty or the materials themselves are expensive. The method of producing the desired optically active compound by utilizing enzymatic reaction or other reaction similar thereto by the use of an optically inactive starting material has also had the problem that in many instances it is unsuitable for its industrial application because of a very low substrate concentration or in some instances the final compound obtained can not be said to have a satisfactory optical purity. In addition, in both the methods, they require a long course of steps until the materials are converted to the final end compounds and there are often reaction steps that are difficult to carry out in an industrial scale.

Thus, the conventional processes have had the problem that the compounds having the optically active trimethyl-transdecalin skeleton, including the L-ambrox, can not be produced at a high optical purity in an industrial scale.

SUMMARY OF THE INVENTION

This invention intends to solve the problems involved in the prior art discussed above, and an object thereof is to make it possible to produce an L-ambrox with a high optical purity, at a low cost and in an industrial scale.

Another object of this invention is to make it possible to produce compounds having the optically active trimethyl-transdecalin skeleton, including the L-ambrox, at a high optical purity in an industrial scale and at a low cost and, for this purpose, to make it possible to obtain (−)HC acid or (+)HC acid usable as a synthesis material for the compounds, from an optically inactive (±)HC acid by optical resolution in a good efficiency in an industrial scale.

The objects of this invention can be achieved by the invention described below.

This invention provides a process for producing (−)-3a,6,6,9a-tetramethyl-dodecahydronaphtho[2,1-b]furan, wherein the process comprises the steps of;
subjecting (−)-2,5,5,8a-tetramethyl-1-(carboxymethyl)-2-hydroxydecalin to lactonization by dehydration to form decahydro-3a,6,6,9a-tetramethyl-(3aα,5aβ,9aα,9bβ)-(+)-naphtho[2,1-b]furan-2(1H)-one;
reducing the lactonized compound to convert it into (−)-2,5,5,8a-tetramethyl-1-(hydroxyethyl)-2-hydroxydecalin; and
subjecting the reduced compound to dehydrative cyclization to give (−)-3a,6,6,9a-tetramethyl-dodecahydronaphtho[2,1-b]furan.

This invention also provides a process for optically resolving (±)-2,5,5,8a-tetramethyl-1-(carboxymethyl)-2-hydroxydecalin into optically active (−)-form and (+)-form thereof, wherein said (±)-2,5,5,8a-tetramethyl-1-(carboxymethyl)-2-hydroxydecalin is allowed to react with an optically resolving agent comprising an optically active 1-(aryl)ethylamine, to form a diastereomer.

DETAILED DESCRIPTION OF THE INVENTION

In the process for producing an L-ambrox according to the present invention, those produced by various methods can be used as the synthesis starting material (−)HC acid. For example, it is possible to use those produced by utilizing, e.g., a method in which β-monocyclohomofarnesic acid derived by the Wittig reaction in which dihydro-β-ionone obtained by partially hydrogenating readily available β-ionone is reacted with β-carboxyethyl triphenylphosphonium chloride is cyclized with an acid catalyst (Japanese Patent Application Laid-open No. 57-145869). From the viewpoint of producing the L-ambrox at a low cost and in an industrial scale, it is very preferable to use as the starting material a (−)HC acid produced in the following way.

An industrially available β-ionone of Formula (2) is partially hydrogenated to form dihydro-β-ionone of Formula (3), and then vinyl magnesium chloride is reacted thereon to convert it into dihydro-β-vinyl-ionol of Formula (4). Next, it is reacted with sodium hydride, and thereafter reacted with a chloroformic acid ester to form a carbonate of Formula (5), followed by reaction to insert carbon monoxide in the presence of a palladium catalyst and then hydrolysis to synthesize β-monocyclohomofarnesic acid of Formula (6). On the β-monocyclohomofarnesic acid obtained, chlorosulfonic acid is reacted to effect cyclization to thereby produce (±)-norambreinolide of Formula (7). This (±)-norambreinolide is hydrolyzed to give a (±)HC acid of Formula (9). Subsequently this (+)HC acid is reacted with an optically active resolving agent to give a (−)HC acid with a high optical purity.

The process for producing the L-ambrox and process for optically resolving the (±)HC acid according to the present invention will be described below with reference to the following reaction scheme which represents the whole synthesis route for the L-ambrox, using the β-ionone as a starting material.

Reaction scheme

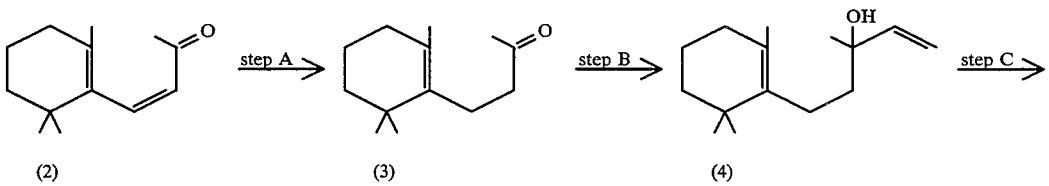

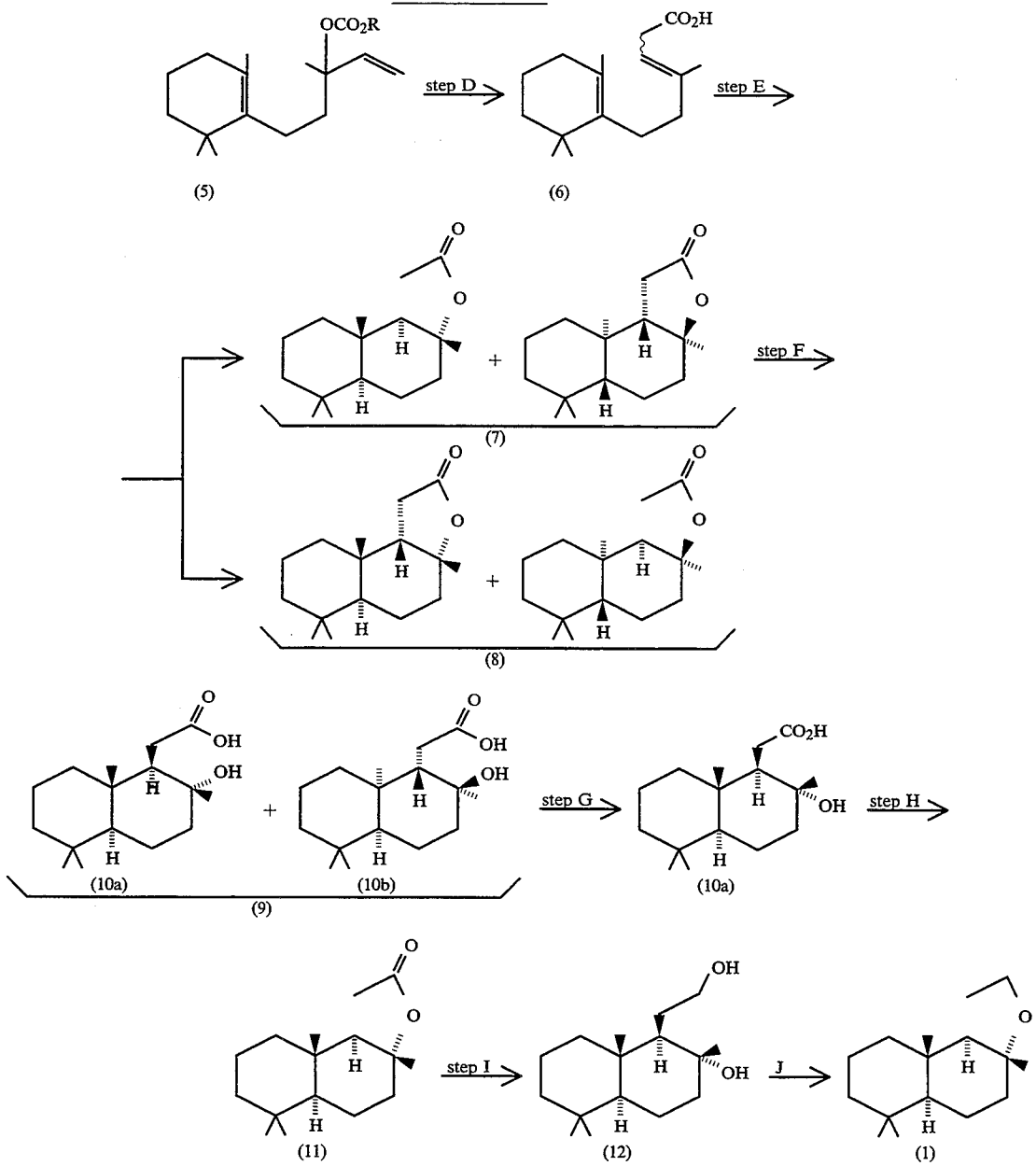

-continued
Reaction scheme

Step A

First, the β-ionone of Formula (2) is reduced to the dihydro-β-ionone of Formula (3). In this case, various methods can be applied in order to selectively reduce only the double bond at the α,β-position of the carbonyl group. In view of readiness in operation and cost, preferably the β-ionone is hydrogenated in a solvent in the presence of a nickel diatomaceous earth catalyst. In such an instance, the nickel diatomaceous earth catalyst may be used in an amount of from 0.5 to 50% by weight preferably from 0.8 to 5% by weight, and more preferably 1% by weight, based on β-ionone.

In this reduction reaction, a solvent may preferably be used. The solvent for that purpose may include aliphatic alcohols such as methanol, ethanol and n-propanol. In particular, it is preferred to use ethanol. Besides these, ether compounds such as tetrahydrofuran and dioxane may also be used. The amount of such a solvent used may vary depending on the type of the solvent. In usual instances, the solvent may preferably be used in an amount of from 20 to 90% by weight, and more preferably from 30 to 50% by weight, based on β-ionone.

Hydrogen pressure applied when this reduction reaction is carried out may also vary depending on the amount of the catalyst used, the type of the solvent and the reaction temperature. In usual instances, it may be from 1 to 100 atmospheric pressure, preferably from 5 to 20 atmospheric pressure, and more preferably from 8 to 12 atmospheric pressure. The reaction temperature may usually be from 20° to 150° C., preferably from 60° to 100° C., and more preferably from 75° to 80° C. The reaction time may also vary depending on the type of the solvent used and the pressure of hydrogen. It may preferably be from 10 to 20 hours. Upon catalytic hydrogenation of the β-ionone thus carried out in the presence of the nickel diatomaceous earth catalyst, the dihydro-β-ionone can be obtained in a high yield (usually from 85 to 95%).

Step B

The dihydro-β-ionone of Formula (3) obtained in the step A is reacted with a slightly excess amount of $CH_2=CHMgX$ (wherein X is a halogen such as chlorine or bromine) in a solvent to form the dihydro-β-vinyl-ionol of Formula (4). In this step, the solvent may include ethereal solvents such as diethyl ether, tetrahydrofuran and diethylene glycol dimethyl ether. Tetrahydrofuran may preferably be used. The reaction conditions may vary depending on, e.g., the type of the solvent used. In usual instances, the reaction may be carried out at 0° to 100° C., and preferably about 15° to 25° C., for 1 to 5 hours. Thereafter, the reaction solution is poured into an aqueous solution of a mineral acid such as hydrochloric acid or sulfuric acid, followed by extraction, separation and treatment of the organic layer by conventional methods. Thus the dihydro-β-vinyl-ionol can be obtained in a high yield (about 85%) based on dihydro-β-ionone.

In the case when a low-boiling solvent as exemplified by tetrahydrofuran is used as the solvent, the $CH_2=CHMgX$ is reacted on the dihydro-β-ionone and thereafter an aromatic hydrocarbon type solvent such as benzene, toluene or xylene, preferably toluene, is added in the reaction vessel, followed by gradual heating to evaporate tetrahydrofuran. The reaction vessel is heated to 100° C. and the greater part of tetrahydrofuran is evaporated. Thereafter the reaction solution is cooled to room temperature and then poured into the aqueous solution of a mineral acid such as hydrochloric acid or sulfuric acid. Thus the tetrahydrofuran can be recovered without inclusion of water.

Step C

From the dihydro-β-vinyl-ionol of Formula (4) obtained in the step B, its hydroxyl group is formed into a carbonate using a halogenated formic acid ester such as ethyl chloroformate, to form the dihydro-β-vinyl-ionol carbonic acid ester of Formula (5) (in the formula, R is an aliphatic alkyl group such as methyl or ethyl). In this case, before the formation into the carbonate, the ethyl chloroformate or the like may preferably be reacted after the hydroxyl group or the dihydro-β-vinyl-ionol has been formed into a sodium alkoxide using a hydride of an alkali metal as exemplified by sodium hydride.

More specifically, the dihydro-β-vinyl-ionol is reacted under reflux of a slightly excess amount of sodium hydride in an ethereal solvent such as tetrahydrofuran or an aromatic hydrocarbon solvent such as benzene or toluene, and preferably in toluene, followed by cooling to 0° to 5° C. Thereafter, the halogenated formic acid ester is added to the reaction solution, and the temperature is raised to room temperature to complete the reaction. The resulting reaction mixture is poured into water under ice cooling to carry out extraction with a hydrocarbon type solvent, followed by separation and treatment by conventional methods. Thus the carbonate of dihydro-β-vinyl-ionol can be substantially quantitatively obtained.

Step D

The carbonate of dihydro-β-vinyl-ionol of Formula (5) obtained in the step C is reacted with carbon monoxide in the presence of a palladium catalyst to form β-monocyclohomofarnesic acid of Formula (6). The palladium catalyst used may include divalent salts such as palladium acetate and palladium chloride, complexes having a valence of 0 such as palladium tetrakis(triphenylphosphine), and supported catalysts such as palladium carbon and palladium alumina. In particular, palladium carbon is preferred, which can be readily recovered by an industrial means. The amount of the palladium catalyst used may vary depending on the type of the catalyst. In usual instances, the catalyst may be used in an amount of from 0.01 to 50% by weight, preferably from 2 to 10% by weight and more preferably from 4 to 6% by weight, based on the carbonate of dihydro-β-vinyl-ionol.

A compound serving as a ligand may include two-ligand type compounds such as substituted or unsubstituted triarylphosphines, trialkylphosphines and 1,2-bis(-diphenylphosphino)ethane, any of which can be used. Tri-orthotriphosphine is preferably used. The amount of such a compound may vary depending on the type of the palladium catalyst used. In the case when palladium carbon is used as the catalyst, it may be in an amount of from 0.5- to 10-fold mole equivalent weight, and preferably from 3- to 5- fold mole equivalent weight, based on metallic palladium supported on palladium carbon.

In this step D, a solvent may preferably be used. For example, an aliphatic alcohol such as methanol, ethanol or isopropanol, and preferably isopropanol, may be used. Such a solvent may be used usually in an amount of from 0.5 to 10 folds by weight, and preferably from 3 to 7 folds by weight, in approximation, based on the carbonate of dihydro-β-vinyl-ionol.

The reaction is operated in the following way: First, carbon monoxide is introduced into a reaction vessel at a gas pressure of from 1 to 100 atmospheric pressure, and preferably from 40 to 60 atmospheric pressure, and the reaction is carried out at a reaction temperature of from 30° to 100° C., and preferably from 40° to 60° C., for about 5 hours. After the reaction has been completed, the catalyst is filtered off. To the flitrate, an excess amount of aqueous 10 to 50% and preferably 30% solution of an alkali metal hydroxide such as sodium hydroxide is added, followed by heating to a temperature of from 20° to 80° C., and preferably from about 30° to 50° C., to carry out hydrolysis. Thus, according to a conventional method, the β-monocyclohomofarnesic acid can be obtained in a high yield (65 to 75%) based on the carbonate of dihydro-β-vinyl-ionol.

Step E

The β-monocyclohomofarnesic acid of Formula (6) obtained in the step D is subjected to cyclization in the presence of an acid catalyst to form the (±)-norambreinolide of Formula (7). The acid catalyst used may include mineral acids such as hydrochloric acid and sulfuric acid, Lewis acids such as stannous chloride and boron trifluoride etherate, and sulfonic acids such as p-toluenesulfonic acid, fluorosulfonic acid and chlorosulfonic acid, any of which can be used. In particular, in view of cost, safety and cyclization yield, chlorosulfonic acid is preferred as the acid catalyst.

Such an acid catalyst may be used usually in an amount of from 1- to 5-fold mols, and preferably from 1.5- to 2.5-fold mols, based on β-monocyclohomofarnesic acid.

In the presence of such an acid catalyst, the cyclization reaction may be carried out in a solvent including nitroalkanes such as nitromethane and nitropropane, chlorinated hydrocarbons such as dichloromethane and trichloromethane, ethers such as isopropyl ether and tetrahydrofuran or acetonitrile, and preferably in dichloromethane, at a reaction temperature of from −100° to 0° C., and preferably from −80° to −30° C., for about from 0.1 to 1 hour, and preferably from 0.4 to 0.6 hour.

After the reaction has been completed, the reaction solution is poured into water, and the organic layer is extracted with a solvent such as dichloromethane, followed by treatment by a conventional method to give a crude product, which is then recrystallized using a hydrocarbon type solvent such as n-hexane or n-heptane. Thus the (±)-norambreinolide can be obtained in a high yield (about 85%). In this instance, (±)-9-epi-norambreinolide of Formula (8) is formed as a by-product. The proportion of formation of the both depends on the stereochemistry of the double bond at the $\beta,\gamma$-position of the carboxylic acid of the $\beta$-monocyclohomofarnesic acid, where the (±)-norambreinolide is formed from its trans-form, and the (±)-9-epi-norambreinolide from its cis-form. The proportion of the both is usually such that the (±)-norambreinolide is 60 to 65% and the (±)-9-epi-norambreinolide is 35 to 40%.

Step F

The (±)-norambreinolide of Formula (7) obtained in the step E is hydrolyzed to produce (±)-2,5,5,8a-tetramethyl-1-(carboxymethyl)-2-hydroxydecalin (hereinafter "(±)HC acid") of Formula (9), which is a mixture of the (−)HC acid of Formula (10a) and the (+)HC acid of Formula (10b). Since the (±)-norambreinolide obtained in the step E contains the (±)-9-epi-norambreinolide as an impurity, the both must be separated. This separation may be made by fractional recrystallization or column chromatography. Alternatively, based on the fact that simple alkaline hydrolysis of the both results in hydrolysis of only the (±)-norambreinolide, the separation of the both and the formation of the (±)HC acid may be simultaneously carried out by a simple method described below.

That is, the mixture of the (±)-norambreinolide and (±)-9-epi-norambreinolide is dissolved in 1- to 20-fold by weight, and preferably 5-fold by weight, of aliphatic lower alcohol such as methanol or ethanol, and thereafter an excess mole weight and preferably 2- to 5-fold mole equivalent weight of aqueous 10 to 50% and preferably 30% solution of alkali metal hydroxide such as sodium hydroxide or potassium hydroxide is added to carry out hydrolysis for about 5 hours preferably under conditions of 60° to 70° C. or reflux. Under such conditions, the (±)-norambreinolide is selectively hydrolyzed and formed into a salt of (±)HC acid. On the other hand, the (±)-9-epi-norambreinolide is hardly hydrolyzed under such conditions. In the subsequent procedure, the both may be separated according to a conventional method. For example, the reaction solution after the hydrolysis is cooled to room temperature, followed by addition of an extraction solvent including hydrocarbons such as n-hexane and n-heptane and aliphatic ethers such as diethyl ether and diisopropyl ether, to extract the unreacted (±)-9-epi-norambreinolide. To the remaining aqueous layer, an aqueous solution of a mineral acid such as sulfuric acid or hydrochloric acid is added under ice cooling to give a free (±)HC acid, which is then extracted with a solvent including aliphatic hydrocarbons, aliphatic ethers and acetic esters, followed by treatment by a conventional method. Thus an (±)HC acid with a high purity can be obtained.

Step G

Next, the (±)HC acid of Formula (9) obtained in the step F is reacted with a resolving agent, optically active 1-(aryl)ethylamine to form two kinds of diastereomer salts corresponding to (+)HC acid and (−)HC acid. In this case, the reaction may preferably be carried out by dissolving, with heating, the (±)HC acid and resolving agent in a solvent.

The optically active 1-(aryl)ethylamine used in this reaction as a resolving agent may include various amines, any of which can be used. In view of their availability and readiness for the formation of the diastereomer salts, (±)- or (−)-1-(p-tolyl)ethylamine or (+)- or (−)-1-(α-naphthyl)ethylamine is preferred. There are no particular limitations on the molar ratio of the (±)HC acid to the resolving agent. In order to carry out the optical resolution in a good efficiency and at a high purity, the resolving agent may preferably be used in 0.4 to 1.0 mole equivalent weight based on the weight of the (±)HC acid.

The solvent that can be used may include C1 to C6 and preferably C1 to C4 alcohols such as methanol, ethanol, n-propanol, isopropanol and n-butanol, C3 to C5 alkyl ketones such as acetone and methyl isobutyl ketone, ethers such as dioxane, tetrahydrofuran and tetrahydropyran, water, or a mixture of these, aromatic hydrocarbons such as benzene, toluene and xylene, C3 to C8 cyclalkanes such as cyclohexane, and alkanes such as n-hexane, n-heptane, n-octane and n-decane. In particular, in order to obtain optically active (+)HC acid or (−)HC acid with a high purity, a water and methanol mixed solvent or dioxane may preferably be used as the solvent.

In the case when water is used as the solvent, an optically active (+)HC acid or (−)HC acid with a higher purity can be obtained since the diastereomer salts can be neutralized after their formation, using the unreacted (±)HC acid and an alkali hydroxide such as sodium hydroxide or potassium hydroxide or a base such as ammonia.

The amount of the solvent used may vary depending on the type of the resolving agent, the type of the solvent, the solubility of the diastereomer salts and so forth. It may be used in an amount of from 1 to 20 liters per mol of resolving agent in the case when the optically active 1-(p-tolyl)ethylamine or 1-(α-naphthyl)ethylamine is used as the resolving agent.

In the case when the resolving agent used is the (+)-1-(aryl)ethylamine, the diastereomer salts obtained are two kinds of compounds, [(+)HC acid.(+)-1-(aryl)ethylamine]salt and [(−)HC acid.(+)-1-(aryl)ethylamine]salt, corresponding to the (+)HC acid and the (−)HC acid, respectively. In the case when the resolving agent used is the (−)-1-(aryl)ethylamine, two kinds of diastereomer salts, [(+)HC acid.(−)-1-(aryl)ethylamine] salt and [(−)HC acid.(−)-1-(aryl)ethylamine] salt, corresponding to the (+)HC acid and (−)HC acid, respectively.

Next, the two kinds of diastereomer salts are separated by a conventional method. For example, they can be separated by utilizing a difference in the solubility of the diastereomer salts in the solvent. In such a case, it is preferred that the reaction solution is cooled to a given crystallization temperature into a state of saturation and this state is maintained so that only one part, a more slightly soluble diastereomer salt, can be crystallized from the reaction solution in which the diastereomer salts have been formed. The crystallization temperature may vary depending on the type or amount of the solvent, the difference in solubility of the diastereomer salts. From an economical viewpoint, it may be in the range of from −20° to +50° C. When the one-part diastereomer salt is crystallized, a small quantity of diastereomer salt thereof may preferably be added to the reaction solution as seed crystals. The diastereomer salt crystallized can be isolated by a commonly available method such as filtration or centrifugal separation.

Finally, the diastereomer salt obtained is formed into a free carboxylic acid by a conventional method, so that the desired (+)HC acid or (−)HC acid can be obtained. For example, the diastereomer salt is dissolved in a mixed solvent of water and a solvent such as methanol, followed by addition of an acid including mineral acids such as hydrochloric acid, sulfuric acid and phosphoric acid and sulfonic acids such as p-toluene sulfonic acid to make the diastereomer salt solution acidic. Thus the (+)HC acid or (−)HC acid having a free carboxylic acid can be formed, which is then extracted with a solvent such as ethyl acetate, and washed, followed by removal of the solvent to give (+)HC acid or (−)HC acid with a high purity. If necessary, in order to recover the optically active resolving agent, the diastereomer salt solution may be made alkaline using a base such as sodium hydroxide, potassium hydroxide or sodium methoxide before the solution is made acidic, and thereafter the optically active resolving agent may be recovered and removed using an extraction solvent such as ether. Alternatively, such recovery operation may be carried out on the aqueous residual solution from which the (+)HC acid or (−)HC acid has been extracted by adding acid.

The optical purity of the diastereomer salt thus separated can be determined by a conventional method. For example, it can be determined from data of specific rotation or NMR in the manner as described below.

Determination of optical purity from specific rotation:

The diastereomer salt which is a salt with (−)-form 1-(p-tolyl)ethylamine is dissolved in methanol and its angle of rotation is measured. Separately therefrom, the specific rotation of a salt with (−)-form 1-(p-tolyl)ethylamine, of (−)HC acid {$[\alpha]_D^{29}$ −3.17° (c=0.50, methanol)} derived from naturally occurring sclareol is measured. As a result, the optical purity can be determined by comparing {$[\alpha]_D^{30}$+16.18° (c=1.00)} with the specific rotation of the diastereomer salt previously obtained.

Determination of optical purity by NMR spectroscopy:

First, as a preliminary step of measurement, an equimolar amount of (−)-form 1-(α-naphthyl)ethylamine is reacted on optically inactive hydroxycarboxylic acid to form a salt, which is then dissolved in chloroform-d, and proton NMR is measured to confirm that the signals of a methyl group separated in a 1:1 ratio, originating from diastereomer are present at $\beta$=1.12 ppm and $\beta$=1.15 ppm. NMR data of a salt comprised of (−)HC acid derived from naturally occurring sclareol and (−)-form 1-(α-naphthyl)ethylamine are also obtained to confirm that only the signal of $\delta$=1.12 ppm is present. This signal originates from the methyl group at the C8-position as shown below.

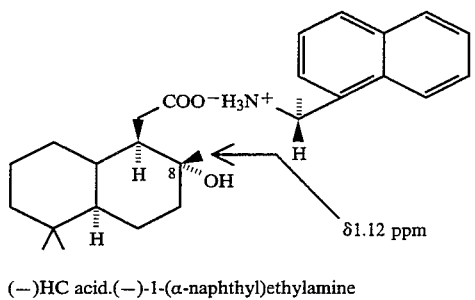

(−)HC acid.(−)-1-(α-naphthyl)ethylamine

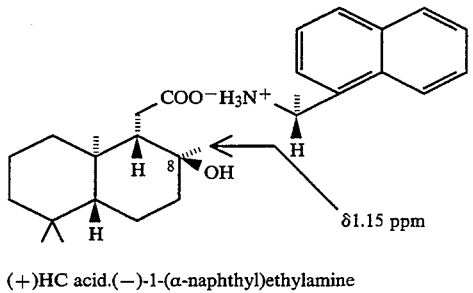

(+)HC acid.(−)-1-(α-naphthyl)ethylamine

Based on such facts, NMR of the diastereomer salt obtained in the present invention is next measured, and the optical purity can be determined from the relative intensity of the signals of $\delta$=1.12 ppm and $\delta$=1.15 ppm.

Step H

The (−)HC acid of Formula (10) obtained in the step G is lactonized according to a conventional method to form (+)-norambreinolide of Formula (11). For example, the (−)HC acid is dissolved in an aromatic hydrocarbon solvent such as toluene or xylene and the solution is heated and refluxed, followed by removal of water produced. Thus the (+)-norambreinolide can be formed.

Step I

The (+)-norambreinolide of Formula (10)obtained in the step H is usually reduced in a solvent to form (−)-2,5,5,8a-tetramethyl-1-(hydroxyethyl)-2-hydroxydecalin (hereinafter "(−)-diol").

A reducing agent used in this step may be appropriately selected from reducing agents capable of opening the lactone ring to form a diol, and put into use. For example, metal hydride compounds of aluminum compounds such as bis-(2-methoxy-ethoxy)-aluminum sodium hydride, aluminum lithium hydride and diisobutylaluminum hydride can be preferably used. The reducing agent may be used in an amount that becomes slightly excess to the equimolar amount, with respect to the (+)-norambreinolide. The reaction temperature may vary depending on the type of the reducing agent used. In usual instances, it may be in the range of from 20° to 80° C.

The solvent used in this step can be exemplified by ethers such as ether and tetrahydrofuran and aromatic hydrocarbons such as benzene, toluene and xylene.

After the reducing reaction has been completed, a post-treatment may be made according to a conventional method. For example, the reaction mixture is poured into an aqueous solution of a mineral acid such as hydrochloric acid or sulfuric acid under ice cooling, followed by extraction with a hydrocarbon type solvent such as n-hexane. The extract is washed with an aqueous sodium hydrogencarbonate solution, and thereafter washed with water until the aqueous layer turns neutral, finally followed by washing with saturated brine and then removal of the solvent.

Step J

The (−)-diol of Formula (12) obtained in the step I is subjected to dehydrative cyclization by a conventional method to give the final compound L-ambrox of Formula (1). For example, the L-ambrox can be obtained by bringing the (−)-diol into contact with p-toluenesulfonyl chloride in the presence of a base.

The base that can be used in the reaction may include nitrogen-containing organic bases such as pyridine, quinoline and triethylamine. This base may be used in an amount, by weight, of from 1 to 10 folds, and preferably about 5 folds, based on the (−)-diol. The p-toluenesulfonyl chloride may be used in an amount of from 1- to 10-fold mol, and preferably about 2-fold mol, based on the (−)-diol. Reaction temperature may vary depending on the type of the base used, and may be in the range of from −20 to +60. Reaction time may vary depending on the type of the base used and the reaction temperature, may be about 2 to 20 hours.

After the reaction has been completed, a treatment may be made by a conventional method. For example, the reaction mixture is poured into water under ice cooling, followed by extraction with a hydrocarbon solvent such as n-hexane. The extract is washed with an aqueous sodium hydrogencarbonate solution, and thereafter washed with water until the aqueous layer turns neutral, finally followed by washing with saturated brine and then removal of the solvent.

In this way, according to the the process of the present invention for producing the L-ambrox, the (−)HC acid is used as the synthesis starting material, and hence the desired steric structure can be maintained up to the final end compound by a simple means. In this case, the (±)HC acid produced using the β-ionone as a starting material through the carbon monoxide inserting reaction carried out in the presence of a palladium catalyst is subjected to optical resolution by the process for optically resolving the (±)HC acid, which is another category of the present invention. When the compound thus obtained is used as the reaction starting material (−)HC acid, there can be no problem in the supply of starting materials and also no heavy metal oxidizing agent, bringing about remarkable advantages in view of cost and industrial means.

EXAMPLES

The present invention will be specifically described below by giving Examples.

Example 1

In a 300 ml autoclave equipped with an agitator, 1.2 g of nickel diatomaceous earth (N-113, available from Nikki Chemical Co., Ltd.) as a catalyst and 80 g of ethanol were charged, and reduction treatment was made at a hydrogen pressure of 10 atmospheric pressure at a temperature of 150° C. for 3 hours, followed by addition of 120 g of β-ionone to carry out hydrogenation reaction at a hydrogen pressure of 10 atmospheric pressure at a temperature of 80° C. for 5 hours.

After the reaction was completed, the catalyst was filtered off, and a residual oil obtained after evaporation of the solvent form the filtrate was distilled under reduced pressure to give 115.6 g of dihydro-β-ionone (boiling point: 70°–72° C./0.4 Torr; purity: 94.0%; yield: 89.6%).

Data of its $^1$HNMR and $^{13}$CNMR are as follows:
$^1$HNMR (300 MHz, CDCl$_3$):
δ0.885 (s, 6H, 2×CH$_3$), 1.28–1.35 (m, 2H, CH$_2$), 1.473 (s, 3H, CH$_3$), 1.42–1.52 (m, 2H, CH$_2$), 1.806(t, J=6.0 Hz, 2H, CH$_2$), 2.045 (s, 3H, CH$_3$), 2.10–2.20 (m, 2H, CH$_2$), 2.36–2.44 (m, 2H, CH$_2$).
$^{13}$CNMR (75.5 MHz, CDCl$_3$):
δ19.2 (t), 19.5 (q), 22.0 (t), 28.2 (2×q), 29.5 (q), 32.5 (t), 34.8 (s), 39.5 (t), 44.3 (t), 127.5 (s), 135.7 (s), 208.4 (s).

Example 2

A solution of 800 ml of tetrahydrofuran containing 45.47 g (0.525 mol) of vinyl magnesium chloride was ice-cooled, and 103.2 g of the dihydro-β-ionone (purity: 94.0%, 0.50 mol) obtained in Example 1 was dropwise added thereto in a nitrogen atmosphere within a temperature range of 15° to 20° C. over a period of about 1 hour.

After the addition, 1,000 ml of toluene was added to the reaction solution, followed by gradual heating, and while the tetrahydrofuran was distilled off the heating was continued until the temperature of the reaction solution reached 100° C. After the greater part of the tetrahydrofuran was recovered, the reaction solution was cooled to room temperature, and the reaction mixture was poured into 600 g of ice-cooled aqueous 5% sulfuric acid solution, followed by extraction with toluene. The toluene layer was washed with an aqueous sodium hydrogencarbonate solution, further washed until the aqueous layer turned neutral and finally washed with saturated brine. The toluene was evaporated according to a conventional method, and the residue was distilled under reduced pressure to give 99.3 g of dihydro-β-vinyl-ionol (boiling point: 82°–83° C./0.4 Torr, purity: 95.0%; yield: 85.04).

Data of its $^1$HNMR and $^{13}$CNMR are as follows:
$^1$HNMR (300 MHz, CDCl$_3$): δ0.944 (s, 6H, 2×CH$_3$), 1.262(s, 3H, CH$_3$), 1.32–1.40 (m, 2H), 1.538 (s, 3H, CH$_3$), 1.45–1.60 (m, 4H), 1.852 (t, J=6.0 Hz, 2H, CH$_2$), 1.90–2.10 (m, 2H), 5.03 (d, J=10.8 Hz, 1H), 5.20 (d, J=17.3 Hz, 1H), 5.91 (dd, J=10.8, 17.3 Hz, 1H).
$^{13}$CNMR (75.5 MHz, CDCl$_3$): δ19.4 (t), 19.6 (q), 22.6 (t), 27.3 (q), 28.5 (2×q), 32.6 (t), 34.9 (s), 39.7 (t), 42.2 (t), 73.3 (s), 111.6 (t), 126.7 (s), 136.5 (s), 144.8 (d).

Example 3

In 800 ml of toluene, 16.8 g of sodium hydride (60% product, 0.42 mol) was added in a nitrogen atmosphere, and then 93.5 g of the dihydro-β-vinyl-ionol (purity 95%, 0.40 mol) obtained in Example 2 was added at room temperature to carry out reaction under reflux for 10 hours.

Next, 39.7 g (0.42 mol) of methyl chloroformate was added at 0° to 5° C., followed by stirring at room temperature for 2 hours. The resulting reaction solution was poured into 1,000 ml of water under ice cooling. Thereafter the organic layer was extracted with toluene, further washed until the aqueous layer turned neutral and finally washed with saturated brine, followed by removal of the solvent to give 113.5 g of methyl carbonate of dihydro-β-vinyl-ionol (purity: 96.34; yield: 96.34).

Data of its $^1$HNMR are as follows:
$^1$HNMR (300 MHz, CDCl$_3$): δ0.973 (s, 6H, 2×CH$_3$), 1.37–1.43 (m, 2H), 1.572 (s, 3H, CH$_3$), 1.602 (s, 3H, CH$_3$), 1.50–1.60 (m, 2H), 1.80–2.05 (m, 4H), 5.20 (d, J=11 Hz, 1H), 5.24 (d, J=18 Hz, 1H), 6.04 (dd, J=11,18 Hz, 1H).

Example 4

In a 300 ml autoclave, 58.9 g of the methyl carbonate of dihydro-β-vinyl-ionol (purity: 95%, 0.2 mol) obtained in Example 3, 0.85 g of palladium carbon (5%-supported product, 0.4 mmol), 0.487 g (1.6 mmol) of tri-orthotolyl-phosphine and 120 g of isopropanol were charged, followed by stirring for 5 hours under conditions of a temperature range of 50° to 60° C. and a carbon monoxide pressure of 50 atmospheric pressure.

After the reaction was completed, the reaction mixture was taken out of the autoclave, the catalyst was filtered off and then 60 g of aqueous 30% sodium hydroxide solution was added to the filtrate, followed by stirring at 40° C. for 2 hours. Thereafter, the reaction solution was cooled to room temperature, and its neutral components were extracted with n-hexane (100 ml×twice). Next, 500 g of aqueous 5% sulfuric acid solution was added under ice cooling to make the reaction solution acidic, followed by extraction by adding n-hexane (200 ml×twice). The n-hexane layer was washed with water until the aqueous layer turned neutral, and finally washed with saturated brine, followed by evaporation of the solvent to give 35.6 g of β-monocyclohomofarnesic acid (yield: 71.2%).

The proportion of isomers on the basis of the double bonds at the β,γ-position of the carboxyl group of the resulting β-monocyclohomofarnesic acid was confirmed by NMR analysis to be cis-form:trans-form=33:67.

Data of its $^1$HNMR are as follows:
$^1$HNMR (300 MHz, CDCl$_3$):

Characteristic signals in the trans-form; 0.996 (s, 6H, 2×CH$_3$), 1.606 (s, 3H, CH$_3$), 1.682 (s, 3H, CH$_3$), 3.08(d, J=7Hz, 2H), 5.35 (t, J=7 Hz, 1H).

Characteristic signals in the cis-form: δ1.014 (s, 6H, 2×CH$_3$), 1.644 (s, 3H, CH$_3$), 1.805 (s, 3H, CH$_3$), 3.12(d, J=7 Hz, 2H), 5.28 (t, J=7 Hz, 1H).

Other signals; 1.38–1.46 (m, 2H), 1.52–1.62 (m, 2H), 1.86–1.96 (m, 2H), 2.05–2.10 (m, 4H).

Example 5

In a nitrogen atmosphere, a 50 ml dichloromethane solution of 25.0 g (0.10 mol) of the β-monocyclohomofarnesic acid obtained in Example 4 was dropwise added to a solution formed of 23.3 g (0.2 mol) of chlorosulfonic acid and 200 ml of dichloromethane, cooled to −60° to −70° C. After the addition was completed, the reaction solution was stirred for 20 minutes and thereafter poured on 500 g of ice, and the organic layer was extracted with dichloromethane. The dichloromethane layer was washed with an aqueous sodium hydrogencarbonate solution, washed with water until the aqueous layer turned neutral, and finally washed with saturated brine, followed by evaporation of the solvent to give a crude norambreinolide, which was further recrystallized with n-hexane. Thus, 20.8 g of crystals of norambreinolide (yield: 83.24) was obtained. The crystals were comprised of a mixture of (±)-norambreinolide and (±)-9-epi-norambreinolide (67:33).

Next, the mixed crystals were dissolved in 100 ml of methanol, and 30 g of 30% sodium hydroxide was added to the solution to carry out hydrolysis under reflux. As a result, the (±)-norambreinolide was selectively hydrolyzed and it moved to the aqueous layer.

From the reaction mixture cooled to room temperature, the (±)-9-epi-norambreinolide not hydrolyzed was separated by extraction with n-hexane (100 ml ×three times). To the remaining aqueous reaction solution, 250 g of aqueous 5% sulfuric acid solution was added under ice cooling to make the solution acidic, followed by extraction with ethyl acetate (100 ml×three times). The organic layer was washed with water until the aqueous layer turned neutral, and finally washed with saturated brine, followed by evaporation of the solvent to give 13.3 g of crystals of (±)HC acid in which the lactone ring of the (±)-norambreinolide was opened, i.e. the (±)-2,5,5,8a-tetramethyl-1-(carboxymethyl)-2-hydroxydecalin in I.U.P.A.C. name. From the n-hexane solution of (±)-9-epi-norambreinolide, 6.80 g of (+)-9-epi-norambreinolide (purity: 96%) was obtained according to a conventional method. These compounds had the following physicochemical properties.

(±)HC acid [I.U.P.A.C. name: (±)-2,5,5,8a-tetramethyl-1-(carboxymethyl)-2-hydroxydecalin]

Melting point: 73°–75° C.
$^1$HNMR (300 MHz, CDCl$_3$): 0.799 (s, 6H, 2×CH$_3$), 0.886 (s, 3H, CH$_3$), 1.172 (s, 3H, CH$_3$), 0.94–1.75 (m, 10H), 1.835 (t, J=6 Hz, 1H), 1.95 (dt, J=3,13 Hz, 1H), 2.34 (dd, J=4,16 Hz, 1H), 2.51 (dd, J=6,16 Hz).
13CNMR (75.5 MHz, CDCl$_3$):
δ15.8 (q), 18.8 (t), 20.8 (t), 21.8 (q), 23.5 (q), 30.5 (t), 33.6 (s), 33.7 (q), 38.9 (s), 39.6 (t), 42.1 (t), 44.7 (t), 56.2 (d), 58.0 (d), 77.9 (s), 180.5 (s).

(±)-Norambreinolide

Melting point: 115°–116° C.
$^1$HNMR (300 MHz, CDCl$_3$): δ0.829 (s, 3H, CH$_3$), 0.876(s, 3H, CH$_3$), 0.904 (s, 3H, CH$_3$), 1.326 (s, 3H, CH$_3$), 0.94–1.91 (m, 10H), 1.96(dd, J=6,14 Hz, 1H), 2.07 (dt, J=3,12 Hz, 1H), 2.22 (dd, J=6,16 Hz, 1H), 2.40 (dd, J=14,16 Hz, 1H).
13CNMR (75.5 MHz, CDCl$_3$): δ15.0 (q), 18.0 (t), 20.5 (t), 20.9 (q), 21.5 (q), 28.7 (t), 33.0 (s), 33.1 (q), 36.0 (s), 38.7 (t), 39.4 (t), 42.1 (t), 56.6 (d), 59.0 (d), 86.3 (s), 176.8 (s).

(±)-9-epi-Norambreinolide

Melting point: 93°–94° C. $^1$HNMR (300 MHz, CDCl$_3$):
δ0.823 (s, 3H, CH$_3$), 0.908 (s, 3H, CH$_3$), 1.101 (s, 3H, CH$_3$), 1.546 (s, 3H, CH$_3$), 1.02–1.68 (m, 10H), 1.95–2.05 (m, 2H), 2.40 (dd, J=8,17 Hz, 1H), 2.62 (dd, J=14,17 Hz, 1H).
13CNMR (75.5 MHz, CDCl$_3$): δ18.0 (t), 19.1 (t), 21.7 (q), 22.7 (q), 27.2 (q), 32.5 (t), 32.7 (S), 33.3 (q), 35.8 (s), 36.9 (t), 38.1 (t), 41.8 (t), 46.4 (d), 56.7 (d), 85.9 (s), 175.5 (s).

Example 6

To 150 ml of dioxane, 1.34 g (5.00 mmol) of the (+)HC acid obtained in Example 5 and 0.54 g (4.00 mmol) of (−)-1-(p-tolyl)ethylamine were added and dissolved with heating, and thereafter the solution was cooled to room temperature, followed by stirring overnight. The crystals precipitated were filtered off to give 0.866 g (2.149 mmol) of (−)HC acid.(−)-1-(p-tolyl)ethylamine salt. Its yield based on the (−)HC acid used was 86.0%, its specific rotation was $[\alpha]_D^{30}$+9.42° (c=1.0, methanol), and optical purity was 58.2%.

This salt was recrystallized from 30 ml of dioxane to give 0.587 g (1.457 mmol) of (−)HC acid.(−)-1-(p-tolyl)ethylamine salt. Its yield based on the (−)HC acid used was 58.2%, its specific rotation was $[\alpha]_D^{30}+15.27°$ (c=1.0, methanol), and optical purity was 94.4%.

To this amine salt, 2.0 ml of aqueous 1N sodium hydroxide solution was added to carry out hydrolysis, followed by extraction with ether to recover the (−)-1-(p-tolyl)ethylamine. To the aqueous layer formed after the extraction with ether, 2.5 ml of 1N hydrochloric acid was added, followed by extraction with ether. The ether layer was dried with anhydrous sodium sulfate, and the ether was removed under reduced pressure to give 0.375 g of (−)HC acid (1.399 mmol; yield: 56.0%).

Example 7

A solution comprised of a mixture of 63 ml of methanol and 40 ml of water, 5.36 g (20.0 mmol) of the (±)HC acid obtained in Example 5, 1.35 g (10.0 mmol) of (−)-1-(p-tolyl)ethylamine and 10 ml (10.0 mmol) of aqueous 1N sodium hydroxide solution were added and dissolved with heating, and thereafter the solution was cooled to room temperature, followed by stirring overnight. The crystals precipitated were filtered to give 2.859 g (7.094 mmol) of (−)HC acid.(−)-1-(p-tolyl)ethylamine salt. Its yield based on the (−)HC acid used was 70.9%, its specific rotation was $[\alpha]_D^{30}+15.66°$ (c=1.0, methanol), and optical purity was 96.8%.

To this amine salt, 10.0 ml of aqueous 1N sodium hydroxide solution was added to carry out hydrolysis, followed by extraction with ether to recover the (−)-1-(p-tolyl)ethylamine. To the aqueous layer formed after the extraction with ether, 12.5 ml of 1N hydrochloric acid was added, followed by extraction with ether. The ether layer was dried with anhydrous sodium sulfate, and the ether was removed under reduced pressure to give 1.825 g of (−)HC acid (6.810 mmol; yield: 68.1%).

Example 8

A solution comprised of a mixture of 32 ml of methanol and 20 ml of water, 2.68 g (10.0 mmol) of the (±)HC acid obtained in Example 5, 0.865 g (5.00 mmol) of (−)-1-(α-naphthyl)ethylamine and 5 ml (5.00 mmol) of aqueous 1N sodium hydroxide solution were added and dissolved with heating, and thereafter the solution was cooled to room temperature, followed by stirring overnight. The crystals precipitated were filtered to give 1.497 g (3.408 mmol) of (−)HC acid.(−)-1-(α-naphthyl)ethylamine salt. Its yield based on the (−)HC acid used was 68.24%, the ratio of (+)HC acid.(−)-1-(α-naphthyl)ethylamine salt to (−)HC acid.(−)-1-(α-naphthyl)ethylamine salt measured by proton NMR spectroscopy was 5.60:94.4, and optical purity was 88.8%.

To this amine salt, 7.0 ml of aqueous 1N sodium hydroxide solution was added to carry out hydrolysis, followed by extraction with ether to recover the (−)-1-(α-naphthyl)ethylamine. To the aqueous layer formed after the extraction with ether, 12.5 ml of 1N hydrochloric acid was added, followed by extraction with ether. The ether layer was dried with anhydrous sodium sulfate, and the ether was removed under reduced pressure to give 0.860 g of (−)HC acid (3.208 mmol; yield: 64.2%).

Example 9

Into a flask fitted with a reflux condenser having a water separator, 26.8 g (0.10 mol) of the (−)HC acid obtained in Example 6, 7 or 8 and 500 ml of toluene were charged, and while the water produced was removed the reaction was carried out under reflux to lactonize the (−)HC acid.

After the reaction was completed, the toluene was removed to give (+)-norambreinolide in a quantitative yield. This compound had the following physicochemical properties.

Melting point: 123-124° C $[\alpha]_D^{28}+46.5°$ (c=1.00, CDCl$_3$)

$^1$HNMR (300 MHz, CDCl$_3$):
δ0.829 (s, 3H, CH$_3$), 0.876(s, 3H, CH$_3$), 0.904 CH (s, 3H, CH$_3$), 1.326 (s, 3H, CH$_3$), 0.94-1.91 (m, 10H), 1.96(dd, J=6,14 Hz, 1H), 2.07 (dt, J=3,12 Hz, 1H), 2.22 (dd, J=6,16 Hz, 1H), 2.40 (dd, J=14,16 Hz, 1H).

$^{13}$CNMR (75.5 MHz, CDCl$_3$): δ15.0 (q), 18.0 (t), 20.5 (t), 20.9 (q), 21.5 (q), 28.7 (t), 33.0 (s), 33.1 (q), 36.0 (q), 38.7 (t), 39.4 (t), 42.1 (t), 56.6 (d), 59.0 (d), 86.3 (s), 176.8 (s).

Example 10

In a solution prepared by diluting 30.3 g of bis-(2-methoxy-ethoxy)-aluminum sodium hydride (a toluene dispersion; content: 70; %, net weight 21.1 g (0.105 mol)) in 50 g of toluene, a solution prepared by dissolving 24.9 g of the (+)-norambreinolide obtained in Example 9 in 65 g of toluene was dropwise added, and the temperature of the reaction solution was raised to a temperature of 60° C., followed by stirring for 2 hours.

After the reaction was completed, the reaction mixture was poured into 350 g of aqueous 5% sulfuric acid solution under ice cooling. The organic layer was extracted with toluene, thereafter washed with an aqueous sodium hydrogencarbonate solution, washed with water until the aqueous layer turned neutral, and finally washed with saturated brine, followed by evaporation of the toluene to give 25.1 g of (−)-diol (yield from (−)HC acid: 98.8%). This compound had the following physicochemical properties.

$[\alpha]_D^{28}-3.40°$ (c=0.50, MeOH)

$^1$HNMR (300 MHz, CDCl$_3$): δ0.785 (s, 6H, 2×CH$_3$), 0.870 (s, 3H, CH$_3$), 0.86-0.950(m, 1H), 1.186 (s, 3H, CH$_3$), 1.07-1.71 (m, 13H), 1.89 (dt, J=12,3 Hz, 1H), 3.10-3.35 (br, 2H, 2×OH), 3.43 (dt, J=10,7 Hz, 1H), 3.77 (dt, J=10,5 Hz, 1H).

$^{13}$CNMR (75.5 MHz, CDCl$_3$): δ15.3 (q), 18.4 (t), 20.4 (t), 21.4 (q), 24.6 (q), 27.8 (t), 33.2 (S), 33.4 (q), 38.9 (S), 39.3 (t), 41.8 (t), 44.2 (t), 56.0 (d), 59.2 (d), 64.0 (t), 73.0 (t).

Example 11

In a reaction vessel, 25.0 g (0.098 mol) of the (−)-diol obtained in Example 10 was dissolved in 120 g of pyridine, and 37.4 g (0.196 mol) of p-toluenesulfonyl chloride was charged under ice cooling, followed by stirring at room temperature for 24 hours. Thereafter, the reaction mixture was poured into 500 ml of water under ice cooling. The organic layer was extracted with n-hexane (300 ml×three times), thereafter washed with an aqueous 5% sulfuric acid solution and an aqueous sodium hydrogencarbonate solution, washed with water until the aqueous layer turned neutral, and finally washed with saturated brine, followed by evaporation of the n-hexane to give 22.8 g of a crude product of L-ambrox. This crude product was distilled in high vacuo to give 16.5 g of L-ambrox with a purity of 98%, having an excellent aroma of an amber (yield from (−)-diol: 71.0%).

This L-ambrox was analyzed using a capillary column for separating optically active substances (CP- Cyclodextrin B-236-M-19, available from Chrompack Co., 0.25 mm diameter × 50 m long; injection temperature: 250° C., column temperature: 120° to 200° C.; temperature rise: 1° C./min.) to confirm that the L-form, i.e., the (−)-form was contained at a percentage of 99% or more. This compound had the following physicochemical properties.

Boiling point: 122°–124° C./0.4 Torr

Melting point: 74°–75° C. $[\alpha]_D^{28} -25.5°$ (c=1.00, CHCl₃)

¹HNMR (300 MHz, CDCl₃): δ0.839 (s, 3H, CH₃), 0.846(s, 3H, CH₃), 0.884 (s, 3H, CH₃), 1.093 (s, 3H, CH₃), 0.90–1.80 (m, 13H), 1.91–1.97 (m, 1H), 3.78–3.96 (m, 2H).

¹³CNMR (75.5 MHz, CDCl₃): δ14.7 (q), 18.1 (t), 20.3 (t), 20.8 (2×q), 22.3 (t), 32.7 (s), 33.3 (q), 35.8 (s), 39.4 (t), 39.6 (t), 42.1 (t), 56.9 (d), 59.8 (d), 64.5 (t), 79.4 (s).

What is claimed is:

1. A process for producing (±)-2,5,5,8a-tetramethyl-1-(carboxymethyl)-2-hydroxydecalin, comprising the steps of:

allowing a carbonate of dihydro-β-vinyl-ionol according to the following formula:

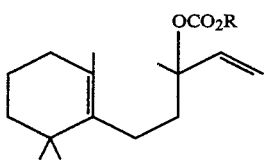

wherein R is an alkyl group, to reach with carbon monoxide in the presence of a palladium catalyst to form β-monocyclohomofarnesic acid;

cyclizing said β-monocyclohomofarnesic acid in the presence of an acid catalyst to form (±)-norambreinolide, according to the following reaction:

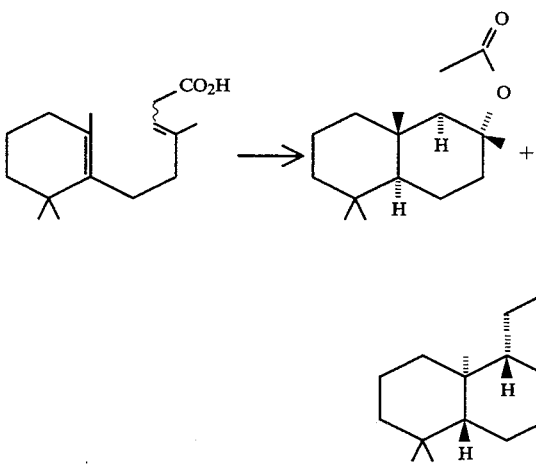

and hydrolyzing said (±)-norambreinolide to form (±)-2,5,5,8a-tetramethyl-1-(carboxymethyl)-2-hydroxydecalin.

2. The method according to claim 1, wherein the palladium catalyst is a divalent salt of palladium.

3. The method according to claim 1, wherein the palladium catalyst is a catalyst comprising zero valence palladium.

4. The method according to claim 1, wherein the palladium catalyst is used in the amount of from 0.001 to 50% by weight based on the carbonate of dihydro-β-vinyl-ionol.

5. The method according to claim 4, wherein the palladium catalyst is used in the amount of from 2 to 10% by weight based on the carbonate of dihydro-β-vinyl-ionol.

6. The method according to claim 5, wherein the palladium catalyst is used in the amount of from 4 to 6% by weight, based on the carbonate of dihydro-β-vinyl-ionol.

7. The method according to claim 1, wherein the palladium catalyst is a supported catalyst.

8. The method according to claim 7, wherein the supported catalyst is palladium carbon.

9. The method according to claim 8, wherein the palladium carbon is present in the amount of from 3- to 5-fold equivalent weight, based on metallic palladium supported on palladium carbon.

10. The method according to claim 1, wherein said carbonate of dihydro-β-vinyl-ionol reacts with carbon monoxide in the presence of a palladium catalyst and a solvent selected from methanol, ethanol, or isopropanol, to form said β-monocyclohomofarnesic acid.

11. The method according to claim 10, wherein said solvent is isopropanol.

12. The method according to claim 10, wherein said solvent is used in the amount of from about 0.5- to 10-fold by weight based on the carbonate of dihydro-β-vinyl-ionol.

13. The method according to claim 10, wherein said solvent is used in the amount of from about 3- to 7-fold by weight based on the carbonate of dihydro-β-vinyl-ionol.

14. The method according to claim 1, further comprising introducing carbon monoxide into a reaction vessel at a gas pressure of from 40 to 60 atmospheres, and then allowing said carbonate of dihydro-β-vinyl-ionol according to formula (5) to react with said carbon monoxide in the presence of a palladium catalyst at a reaction temperature of from 40° to 60° C. to form β-monocyclohomofarnesic acid.

15. The method according to claim 1, wherein said cyclizing of β-monocyclohomofarnesic acid occurs in the presence of an acid catalyst selected from mineral acids, Lewis acids, or sulfonic acids.

16. The method according to claim 15, wherein said acid catalyst is chlorosulfonic acid.

17. The method according to claim 1, wherein said cyclizing of β-monocyclohomofarnesic acid occurs in the presence of an acid catalyst and a solvent, said solvent selected from nitroalkanes, chlorinated hydrocarbons, ethers, or acetonitrile.

18. The method according to claim 17, wherein said solvent is dichloromethane.

* * * * *